United States Patent [19]

Mueller

[11] 3,969,209
[45] July 13, 1976

[54] AUTOMATIC ELECTROCHEMICAL AMBIENT AIR MONITOR FOR CHLORIDE AND CHLORINE

[75] Inventor: Theodore R. Mueller, Oak Ridge, Tenn.

[73] Assignee: The United States of America as represented by the United States Energy Research and Development Administration, Washington, D.C.

[22] Filed: July 8, 1975

[21] Appl. No.: 594,164

[52] U.S. Cl. .......................... 204/195 R; 324/30 R
[51] Int. Cl.² .......................................... G01N 27/46
[58] Field of Search ..................... 204/1 B, 195 R

[56] References Cited
UNITED STATES PATENTS

| | | | |
|---|---|---|---|
| 2,370,871 | 3/1945 | Marks | 204/195 R |
| 2,851,654 | 9/1958 | Haddad | 204/195 R |
| 3,208,926 | 9/1965 | Eckfeldt | 204/1 B |
| 3,413,199 | 11/1968 | Morrow | 204/195 R |
| 3,556,950 | 1/1971 | Dahms | 204/195 R |
| 3,713,994 | 1/1973 | Shults | 204/1 F |
| 3,715,298 | 2/1973 | Goodson et al. | 204/195 R |
| 3,761,376 | 9/1973 | Barstow et al. | 204/1 B |
| 3,761,377 | 9/1973 | Mang | 204/195 R |

Primary Examiner—T. Tung
Attorney, Agent, or Firm—Dean E. Carlson; David S. Zachry; David E. Breeden

[57] ABSTRACT

An electrochemical monitoring system has been provided for determining chloride and chlorine in air at levels of from about 10–1000 parts per billion. The chloride is determined by oxidation to chlorine followed by reduction to chloride in a closed system. Chlorine is determined by direct reduction at a platinum electrode in 6 M $H_2SO_4$ electrolyte. A fully automated system is utilized to (1) acquire and store a value corresponding to electrolyte-containing impurities, (2) subtract this value from that obtained in the presence of air, (3) generate coulometrically a standard sample of chlorine mixed with air sample, and determine it as chlorine and/or chloride, and (4) calculate, display, and store for permanent record the ratio of the signal obtained from the air sample and that obtained with the standard.

6 Claims, 6 Drawing Figures

REVERSIBILITY OF CHLORIDE OXIDATION WAVE AS A FUNCTION OF $(H_2SO_4)$
Plot is the ratio (R) of $(dI/dE)_{peak}/V^{3/2}$ at $V=1.2V/sec$. and at $V=0.3V/sec$.
Theoretical ratio reversible process is unity.

AUTOMATIC ELECTROCHEMICAL AMBIENT AIR MONITOR FOR CHLORIDE AND CHLORINE

This invention was made in the course of, or under, a contract with the Energy Research and Development Administration.

REFERENCE

U.S. Pat. No. 3,713,994, issued Jan. 30, 1973, to Wilbur D. Shults et al. for "Electrochemical Air Pollution Monitoring Device And Method Of Use Thereof," and having a common assignee with the present invention.

BACKGROUND OF THE INVENTION

This invention relates generally to air pollution monitoring systems and more particularly to an automated system for continuous electrochemical monitoring of air pollutants to obtain quantitative measure thereof and maintain permanent record.

As legislation, Such as the Clean Air Act of 1970, is increasingly enacted to define permissible concentrations of pollutant emissions to establish acceptable levels of air pollutants for cities, states, and regions, it becomes increasingly more important to find and develop analytical procedures that are both sensitive and specific for these substances. Then, when more accurate monitoring techniques are made available, standards can be set to limit concentration levels of pollutants in the atmosphere.

In the art, the most widely used instruments for measuring pollutant concentrations in the atmosphere are based upon wet chemical techniques wherein coulometric, colorimetric, or conductometric procedures are utilized. In the coulometric procedure, for example, the pollutant is passed through a collection fluid and a measurement is then made which can be compared with a prior reference measurement. In the standard reference method for nitrogen dioxide, for example, the gaseous sample is bubbled through a solution of sodium hydroxide, where the $NO_2$ is converted to stable sodium nitrate. After collection, the nitrate is diazotized with phosphoric acid, sulfanilamide and coupled to N-1-naphthylethylenediamine; the concentration of the resulting chromophore is then determined colorimetrically.

Recently, monitors based upon such chemical techniques as electrochemical transducers have found increased use by environmental scientists in pollutant detection. These devices depend on selective electrocatalytic oxidation (or reduction) of the pollutants in the cell. In a typical transducer, the sample gas flows past a semipermeable membrane that allows a small, constant fraction to enter the cell. Inside the cell, the sample diffuses through a thin liquid film to an electrocatalytic electrode, where a charge transfer reaction occurs. Bulk electrolyte and a reference electrode make up the rest of the cell. In operation, the cell produces an electrical potential that is directly proportional to the concentration of pollutant in the sample stream and, within limits, is independent of the sample flow rate. The problems involved in determining chlorine and chloride in air with these prior art methods are (1) plugging of the membrane by particulate matter, (2) low collection efficiency which results in poor precision, (3) frequent maintenance schedules are required, and (4) slow response to changes in pollutant levels.

SUMMARY OF THE INVENTION

In view of the above, it is an object of this invention to provide an electrochemical monitor for atmospheric contaminants chlorine and chloride wherein a wide range of such contaminants may be easily and accurately detected.

It is an object of this invention to provide an electrochemical monitor as in the above object which has a response essentially free from interference caused by other species, particularly bromide and iodide.

Yet another object of this invention is to provide an automatic electrochemical monitor for chlorine and chloride which continuously takes representative air samples and automatically measures and records the chloride and chlorine content determined in a closed flow-through electrochemical cell.

Another object of this invention is to provide an automatic electrochemical monitor as set forth in the above objects with the further object of automatic in situ calibration of the device whereby human interaction is not required and wherein the output signal is presented directly in terms of parts per billion of chlorine or chloride.

Yet another object of this invention is to provide an automatic electrochemical monitor for chlorine and chloride wherein maximum sensitivity and selectivity may be achieved with a minimum consumption of chemicals, solution, electrodes, and power.

Other objects and many of the attendant advantages of the present invention will be obvious from the following detailed description taken in conjunction with the accompanying drawings.

BRIEF DESCRIPTION OF THE DRAWINGS

FIG. 5, which consists of FIGS. 5A and 5B, is a block diagram of an automated system for monitoring chlorine and/or chloride from air including the anlayzer shown in FIG. 4 and wherein like reference numerals refer to identical parts shown in FIG. 4.

DETAILED DESCRIPTION

The development of an automatic electrochemical monitor for chlorine ($Cl_2$) and chloride ($Cl^-$) from atmospheric samples which has a fast response with little possibility of interference from other common atmospheric species required the use of inactive metal electrodes to obtain a reasonable degree of reproducibility. In the halogen series of elements, solubility of metallic salts decreases in the order chloride > bromide > iodide. Therefore, it was found that schemes based on collection on an active metal electrode failed to some degree in the presence of other halogens. Selectivity with respect to active gaseous species, such as $SO_2$ and $NO_x$ would also be difficult to achieve within the potential region available. Finally, an investigation of the redox properties of chlorine and chloride at inert electrodes revealed that platinum electrodes can be used in a voltametric measurement system with a $H_2SO_4$ electrolyte produced a highly selective and reversible method for determining chlorine and/or chloride from atmospheric samples, without the interference from the oxidation of water. Experiments indicated that 6 M $H_2SO_4$ was the optimum concentration for the supporting electrolyte. The voltametric experiments further indicated that the oxidation of chloride takes place at approximately 1.28 volts and chlorine reduction takes place at approximately 0.9 volt.

Figure 1:
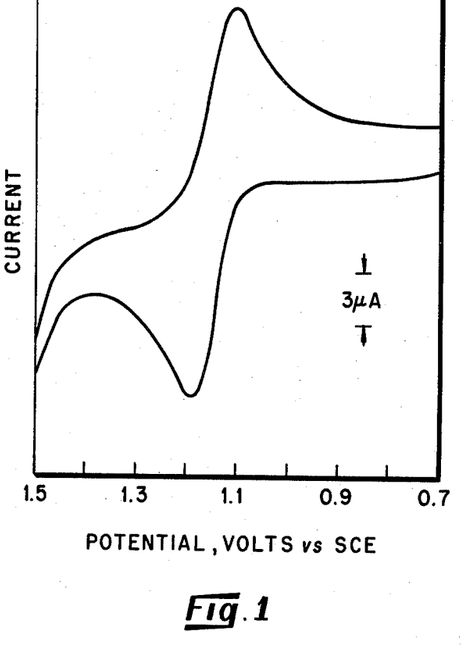
FIG. 1 is a cyclic voltammogram for $10^{-3}$ M chloride in 6 M $H_2SO_4$ at a platinum electrode.
Figure 2:
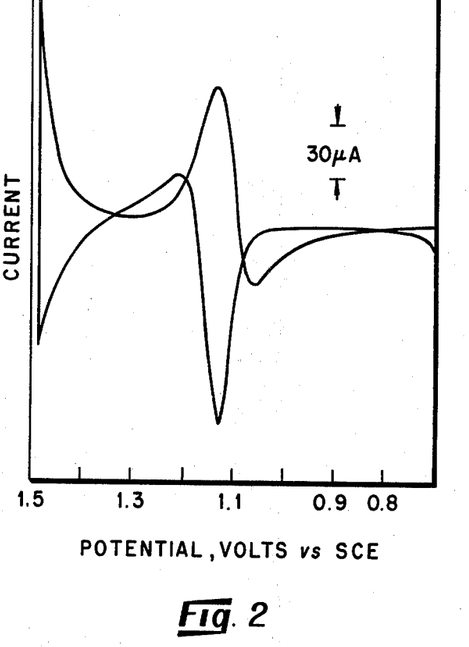
FIG. 2 is a plot of the first derivative of the curve of FIG. 1.
Figure 3:
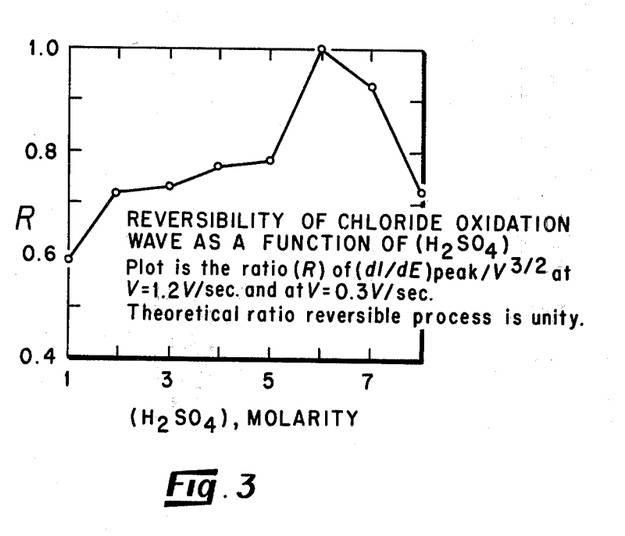
FIG. 3 is a plot of the ratio of first derivative peak potentials as a function of sulfuric acid concentration.

Referring now to FIGS. 1 and 2, wherein FIG. 3 is a cyclic voltammogram for $10^{-3}$ M chloride in 6 M $H_2SO_4$ at a small platinum disk electrode and FIG. 2 is a plot of the first derivative of the curve shown in FIG. 1 recorded simultaneously with that in FIG. 1. The curves show the complete resolution of the chloride-chlorine process from oxygen evolution at high potentials. Referring now to FIG. 3, there is plotted the ratio R of the first derivative peak potentials as a function of sulfuric acid concentration taken from first derivative voltammograms similar to that shown in FIG. 2. FIG. 3 shows that at the 6 M $H_2SO_4$ concentration the chlorine/chloride couple acts most reversibly. It is desirable to operate the monitor under reversible conditions for three reasons. The first is that slight surface contamination of the electrodes has minimum effect on the measured current at a given potential. The second is that selectivity is maximum since the oxidation and reduction potentials can be set at a minimum separation. The third reason, related to the second, is that at any potential more current is measured for a given chlorine or chloride concentration in the electrolyte. In this medium, oxidation of chloride to chlorine is essentially complete at +1.25 volts vs. SCE. At this potential iodide is converted to iodate and bromide to bromate. Since neither of these species is reduced at 0.85 volt, where chlorine reduction is essentially complete, these species do not interfere in a properly executed analysis. Thus, chloride can be determined accurately even in the presence of 1000 fold excess of bromide or iodide.

Figure 4:
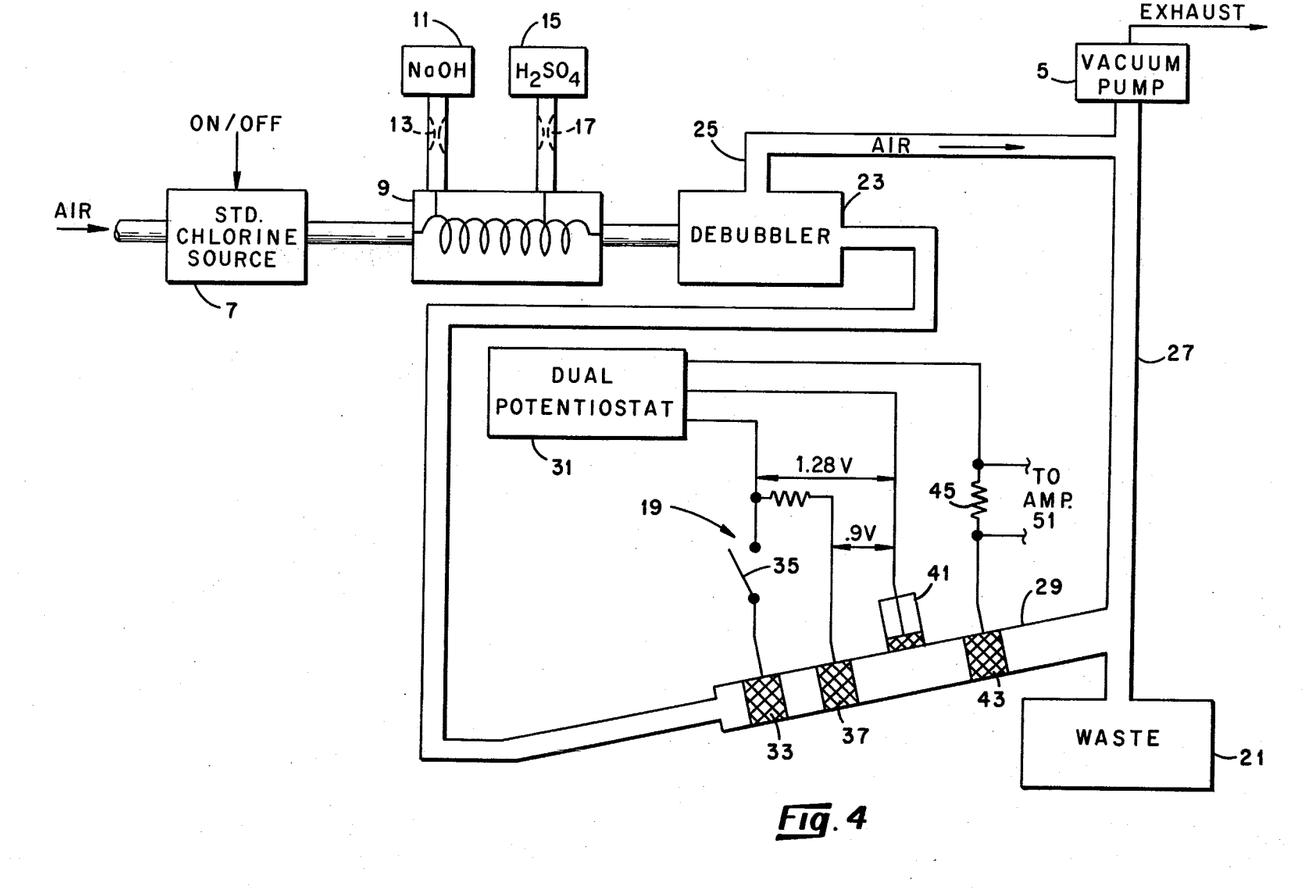
FIG. 4 is a schematic flow diagram of an electrochemical analyzer for monitoring chlorine and/or chloride from atmospheric air according to the present invention.

The monitor may be more readily understood by separating the electrochemistry cell and the electronic readout and process control portion. Referring now to FIG. 4, the electrochemical cell in which the oxidation and reduction measurements are made will be described. Air is drawn into and through the system by means of a vacuum pump 5. The exhaust from the vacuum pump is filtered and then returned to the atmosphere. The air enters the system through a controlled inlet valve, shown in FIG. 5, to a standard chlorine source 7 which, when turned on by the control system, generates chlorine gas at a predetermined rate which is mixed with the entering air. The entering gases flow into an absorber 9. The absorber is preferably a horizontally-mounted, helically-wound coil formed of glass tubing. Dilute sodium hydroxide, about $2 \times 10^{-3}$ M NaOH, is introduced into the front end of the absorber coil from a source 11 through a flow-restricting capillary 13. The sodium hydroxide forms a high surface-to-volume coating in the absorber tubes as it moves through the absorber. The air flow is about 30 ml/sec. Chlorine and hydrogen chloride from the gaseous mixture are sorbed by the NaOH solution. As the solution emerges from the absorber it is mixed with sulfuric acid introduced from a reservoir 15 through a second flow-restricting capillary 17. The flow rate of the sulfuric acid is adjusted to obtain a concentration of about 6 M $H_2SO_4$ in the resulting mixture exiting the absorber 9.

The air/electrolyte solution volume ratio is adjusted to about 1000:1.

It is preferred that the solution is caused to flow through the cell, generally indicated at 19, by means of gravity feed, exiting the cell into an electrolyte waste container 21. In order to prevent bubbles of entrapped air remaining in the cell 19 to disrupt electrochemical measurements, the output of the absorber is introduced into a de-bubbler compartment 23 which has a by-pass exit conduit 25 connected to communicate with the vacuum pump 5 intake. The cell 19 is a flow-through cell slanted upward toward the exit end to accelerate the passage of any air bubbles which may be entrained in the electrolyte to exit via conduit 27, which also communicates with the vacuum pump 5 intake and the waste electrolyte reservoir 21. The flow-through cell 19, which may be constructed from a small section of glass tubing, has a plurality of coiled platinum wire electrodes which are disposed in the flow stream of the electrolyte solution through the cell 19. The electrodes are connected to a dual potentiostat 31 which provides regulated voltages for the selected oxidation-reduction operations.

The first electrode of the cell 19, which the electrolyte contacts, is a conditioning electrode 33 connected to an output of the potentiostat 31 through a switch 35. The switch 35 may be an electronic switch which is controlled from a control line as will be described hereinbelow. The next electrode in the cell is an analytical electrode 37 which is connected to the same output of potentiostat 31 through a resistor 39 which provides a prescribed potential on analytical electrode 35 that is less than the potential applied to the conditioning electrode 33. A standard calomel electrode (SCE) 41 is provided to contact the flowing electrolyte and is connected to the reference output of potentiostat 31. Thus, the voltages on the conditioning electrode 33 and the analytical electrode 37 are referenced from the SCE 41, typically 1.28 volts and 0.9 volt, respectively. The last electrode is a counter electrode 43 which is connected to a third input of potentiostat 31 through a current-sensing resistor 45. The reduction current in the cell flows through counter electrode 43 and through resistor 45. The voltage across resistor 45 is sensed as a signal proportionate to the reduction current and provides the output signal for the cell 19.

Figure 5A:
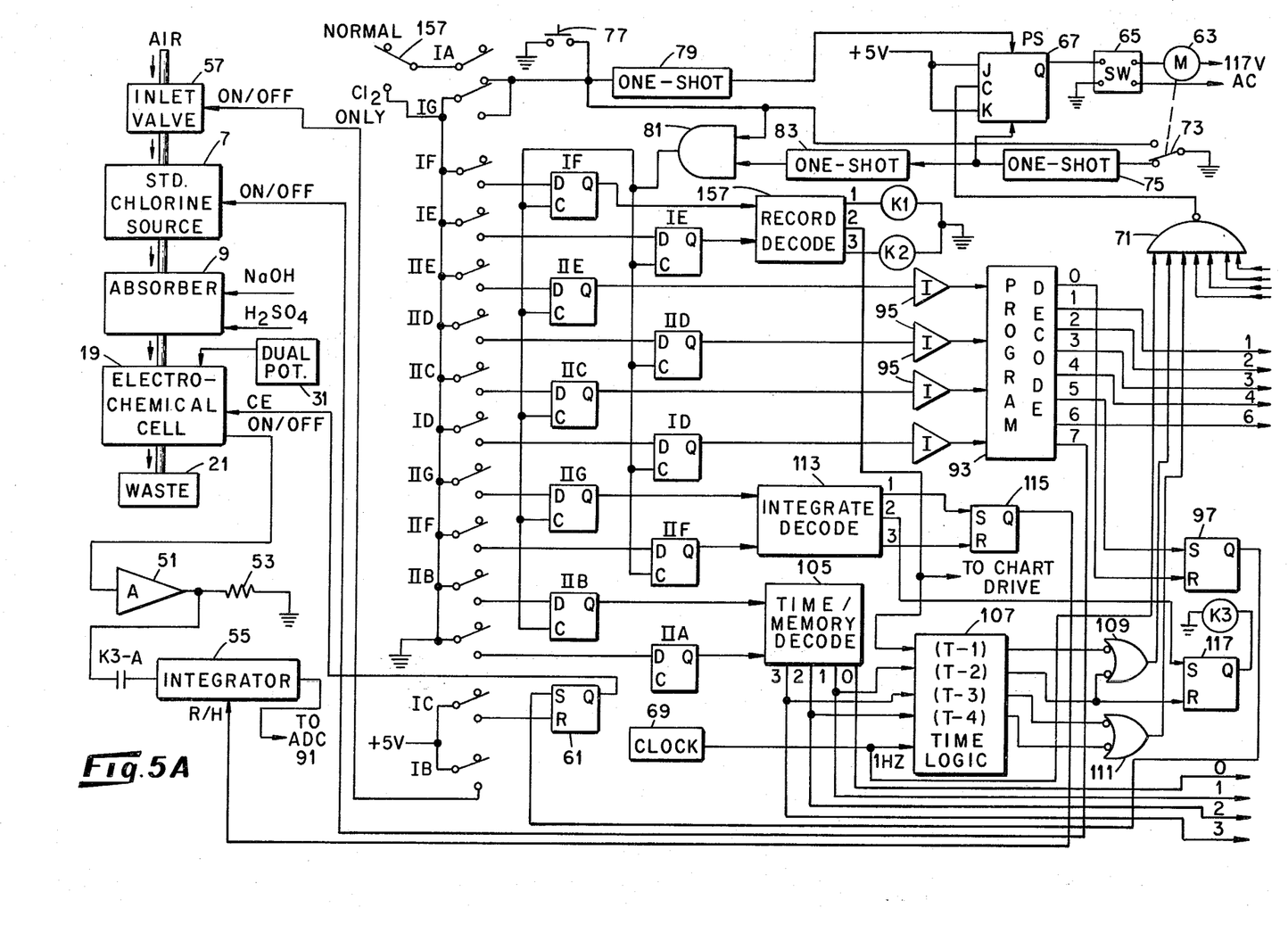

Referring now to FIG. 5A, it will be seen that the voltage signal produced by the flow of reduction current in the cell 19 is fed to the input of an operational amplifier 51 whose output is connected to ground through a load resistor 53. The voltage across resistor 53 is fed through a pair of relay contacts K3 -A to the input of an integrator 55. The reduction current is measured and integrated by integrator 55 under direction from the control circuits as will be described hereinbelow. The integral is converted to digital form and stored in the appropriate buffer storage register in the readout circuitry of FIG. 5B.

Referring again to FIG. 4, it will be seen that when it is desired to measure chlorine in the air, the switch 35 remains open and the conditioning electrode is inactive at this time. The reduction of chlorine at the analytical electrode 37 produces the reduction current which is then integrated over a selected time period and stored. When it is desired to measure chloride, the electrode 33 is switched "on" by closing switch 35 to apply the 1.28 volts thereto and the chloride is oxidized producing chlorine. Subsequently, the chlorine is reduced at the analytical electrode 37 and the current measurement is made during this reduction. This current value is also integrated and the digitized integral is stored in another buffer storage register. The difference in the two currents is the measure of chloride. Once each cycle of operation a known amount of electrochemically-generated chlorine is added by the chlorine source 7 to the incoming air and the integral of the current value resulting from all chlorine reduction is stored in still another buffer storage register. Finally, a correction is made for background impurities in the absence of the air sample. The air inlet valve 57 and the standard chlorine source 7 are both turned "off" so that the background current arising from chloride or other trace impurities in the sulfuric acid and sodium hydroxide electrolyte mixture can be measured. At the 1 part per million analytical level, the background currents are insiginficant fractions of the total current. At the 1 part per billion level, however, background currents may amount to approximately 25% total current. Background measurements are made for both $Cl_2$ and $Cl^-$ and stored in separate memories.

Parts per million chlorine in air is determined by use of the following relationship:

$$\text{Chlorine (PPM)} = \frac{[Cl_2 \text{ in Air} - \text{Background}] \times K_1}{Cl_2 \text{ added} + Cl_2 \text{ in Air} - \text{Bkgd}] - [Cl_2 \text{ in Air} - \text{Bkgd}]}$$

or $$Cl_2 \text{ (PPM)} = \frac{Cl_2 \text{ in Air} \times K_1}{\text{Standard } Cl_2}$$

For chloride analysis, the following relationships apply:

$$\text{Chloride (PPM)} = \frac{[(Cl_2 + Cl^-) \text{ in Air} - \text{Background}] \times K_2}{[Cl_2 \text{ added} + (Cl_2 + Cl^-)\text{Air} - \text{Bkgd}] - [(Cl_2+Cl^-)\text{Air} - \text{Bkgd}] - Cl_2}$$

or $$Cl^- \text{ (PPM)} = (Cl_2 + Cl^-) - Cl_2$$

Figure 5B:
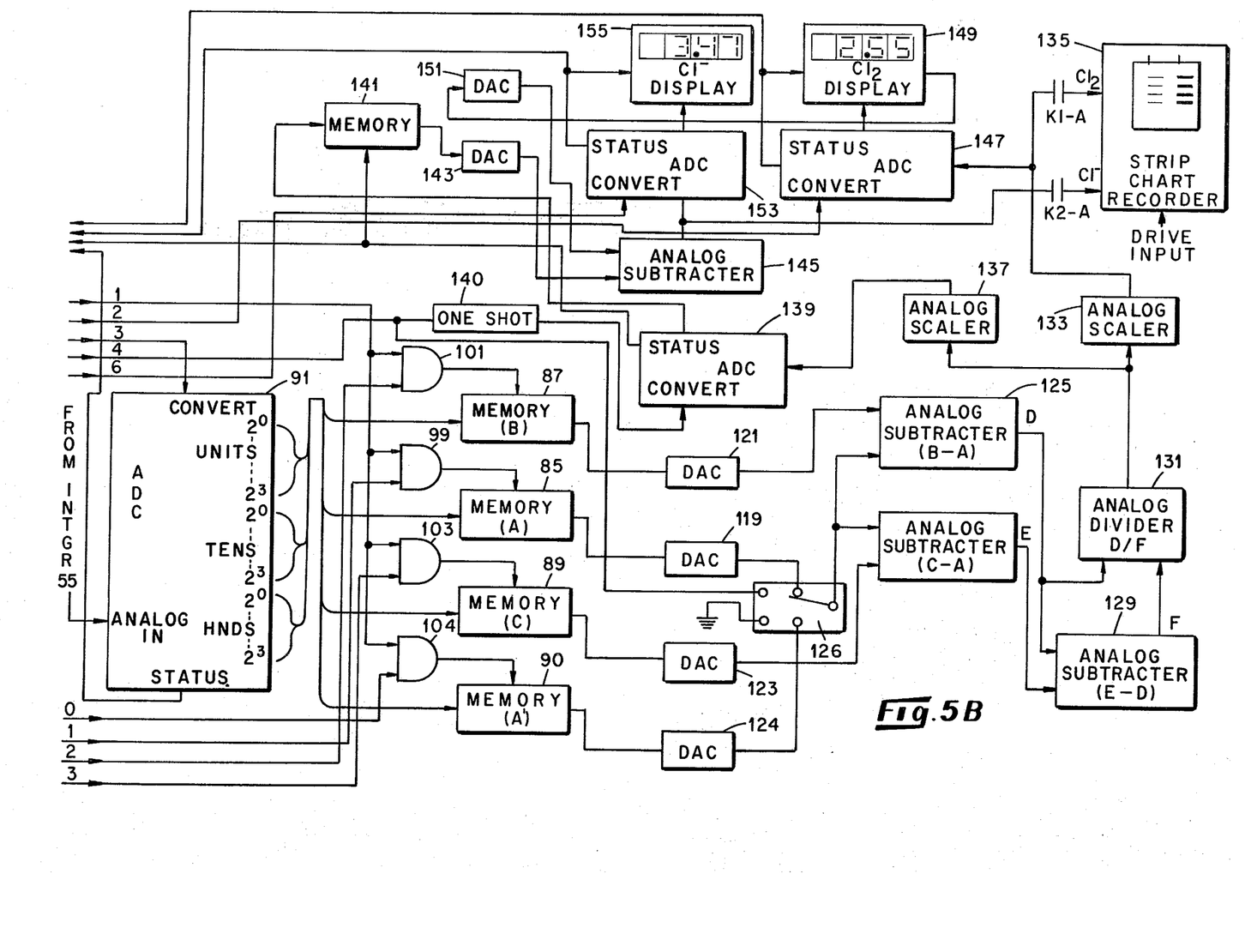

In these equations, $K_1$ and $K_2$ are scaling factors. FIGS. 5A and 5B show schematically the data acquisition and processing system. The sequence of operations is controlled by a drum programmer, not shown. The drum is provided with cams in locations shown in Table I.

TABLE I

|  | Line | Position I A | B | C | D | E | F | G | II A | B | C | D | E | F | G | Operations |
|---|---|---|---|---|---|---|---|---|---|---|---|---|---|---|---|---|
| Home | 0 |  |  | X |  | X |  |  |  |  |  |  |  |  |  | 0. Disconnect Electrode CE |
|  | 1 |  |  |  | X |  |  |  |  |  |  |  |  |  |  | 1. Advance chart; timer 1 |
| Air | 2 |  |  | X |  |  |  |  |  |  | X |  |  |  |  | 2. Generate STD. chlorine |
|  | 3 |  |  |  |  |  |  |  |  |  | X | X |  |  | X | 3. Reset Integrator; delay |
|  | 4 |  |  |  |  |  |  |  |  |  |  |  |  | X |  | 4. Connect integrator input |
|  | 5 |  |  |  |  |  |  |  |  |  |  |  |  |  |  | 5. NOOP |
|  | 6 |  |  |  |  |  |  |  |  |  | X |  |  | X | X | 6. Integrate; timer 2 |
|  | 7 |  | X |  |  |  |  |  |  | X |  |  |  |  |  | 7. ADC 91 Convert |
|  | 8 |  | X |  |  |  |  |  |  |  | X | X | X |  |  | 8. Turn Off Chlorine generator |
|  | 9 |  | X |  |  |  |  |  | X | X | X | X |  |  | X | 9. ADC 91 to Mem. C; Reset Integrator |
|  | 10 |  |  |  |  |  |  |  |  | X | X |  |  |  | X | 10. Delay; Connect integrator |
|  | 11 |  |  |  |  |  |  |  |  |  |  |  |  |  |  | 11. NOOP |
| Air | 12 |  |  |  |  |  |  |  |  | X |  |  |  | X | X | 12. Integrate; timer 2 |
| $Cl_2$ | 13 |  | X |  |  |  |  |  |  | X |  |  |  |  |  | 13. ADC 91 Convert |
|  | 14 |  | X |  |  |  |  |  | X |  | X | X |  |  |  | 14. ADC 91 to Mem. B |
|  | 15 |  |  |  | X |  |  |  |  |  |  |  |  |  |  | 15. Record $Cl_2$ value |
|  | 16 |  | X |  |  |  |  |  |  | X |  |  | X |  |  | 16. ADC 147 Convert |
|  | 17 | X |  |  |  |  |  |  |  |  |  |  |  |  |  | 17. Air Off |
| Bkgd. | 18 | X |  |  |  |  |  |  | X | X |  |  |  |  | X | 18. Air Off; Delay; Reset Integrator |
| $Cl_2$ | 19 | X |  |  |  |  |  |  |  |  |  |  | X |  |  | 19. Air Off; Connect Integrator |
|  | 20 | X |  |  |  |  |  |  | X | X |  |  | X |  | X | 20. Air Off; Integrate; timer 3 |
|  | 21 | X |  |  |  |  |  |  |  |  |  |  |  |  |  | 21. Air Off; NOOP |
|  | 22 | X |  |  |  |  |  |  |  |  |  |  |  |  |  | 22. Air Off; NOOP |
|  | 23 | X | X |  |  |  |  |  |  | X |  |  |  |  |  | 23. Air Off; ADC 91 Convert |
|  | 24 | X | X |  |  |  |  |  | X | X | X |  |  |  | X | 24. Air Off; ADC 91 to Mem. A Reset Integrator |
|  | 25 | X | X |  |  |  |  |  |  |  |  |  |  |  |  | 25. Air Off; Connect Electrode CE |
|  | 26 | X |  |  |  |  |  |  |  |  |  |  |  |  |  | 26. Air Off; NOOP |
|  | 27 | X |  |  |  |  |  |  | X |  |  |  |  |  |  | 27. Air Off; Delay, Timer 2 |
| Bkgd. | 28 | X |  |  |  |  |  |  |  |  |  |  |  |  | X | 28. Air Off; Connect Integrator |
| $Cl^-$ | 29 | X |  |  |  | X |  |  |  | X |  |  |  | X | X | 29. Air Off; Integrate; timer 3 |
|  | 30 | X | X |  |  |  |  |  | X |  |  |  |  |  |  | 30. Air Off; ADC 91 Convert |
|  | 31 | X |  |  |  |  |  |  |  | X | X |  |  |  | X | 31. ADC 1 to Mem. A'; Reset Integrator |
| Air | 32 | X |  |  |  |  |  |  |  |  |  |  |  |  |  | 32. Start Chloride Routine |
| Cl | 33 | X |  | X |  |  |  |  |  |  |  |  |  |  | X | 33. Connect Electrode CE; Reset Integrator |
|  | 34 | X |  |  |  |  |  |  | X | X |  |  |  | X |  | 34. Connect Integrator; delay |
|  | 35 | X |  |  |  |  |  |  |  | X |  |  |  | X | X | 35. Integrate; timer 4 |
|  | 36 | X |  | X |  |  |  |  |  |  | X |  |  |  |  | 36. ADC 91 Convert |
|  | 37 | X |  | X |  |  |  |  | X |  | X | X |  |  | X | 37. ADC 91 to Mem. B; Reset Integrator |
| $Cl_2$+Air | 38 | X |  | X |  |  |  |  |  |  |  | X |  |  |  | 38. Generate STD. Chlorine |
|  | 39 | X |  |  |  |  |  |  |  |  |  |  |  |  |  | 39. NOOP |
|  | 40 | X |  |  |  |  |  |  | X | X |  |  |  |  |  | 40. Delay |
|  | 41 | X |  |  |  |  |  |  |  |  |  |  |  |  | X | 41. Connect Integrator |

TABLE I-continued

| | Line | Position I | | | | | | | Position II | | | | | | | Operations |
|---|---|---|---|---|---|---|---|---|---|---|---|---|---|---|---|---|
| | | A | B | C | D | E | F | G | A | B | C | D | E | F | G | |
| | 42 | X | | | | | | | X | | | | | X | X | 42. Integrate; timer 4 |
| | 43 | X | | X | | | | | | | | X | | | | 43. ADC 91 Convert |
| | 44 | X | | X | | | | | | | X | X | X | X | | 44. ADC 91 to Mem. C |
| | 45 | X | | | | | | | | | | | | | | 45. NOOP |
| Calc. | 46 | X | | X | | | | | | | | | X | X | | 46. ADC 139 Convert |
| Cl⁻ | 47 | X | | | X | | | | | | | | | | | 47. Record SPACE; Advance Chart, Timer 1 |
| | 48 | X | | | | X | X | | | | | | | | | 48. Record Chloride |
| | 49 | X | | | | X | X | | | | | | | | | 49. Record Chloride |
| Go Home | 50 | X | | X | | | | | | | | | X | | | 50. ADC 143 Convert; Home to Line 0 |

These cams operate switches 1A through 11G as shown in FIG. 5A. The switch positions are in turn decoded by means of a digital decoding circuit including a plurality of D.C. flip-flops and binary coded decimal decoders. With the exception of switches 1A, 1B, 1C, and 1G, the normally opened contact thereof is connected to the D input of corresponding numbered D.C. flip-flops. Contacts 1B and 1C, which have their common terminal connected to a +5 volt supply, control, respectively, the air inlet valve 57 and the operation of switch 35 (FIG. 4) to connect and disconnect the conditioning electrode CE in the electrochemical cell 19. Switch 1B has its normally open contact connected to the inlet valve 57 so that when switch 1B is activated by a cam in that position on the drum it is closed, applying the +5 volts to close the air inlet valve 57. Switch 1C has its normally opened contact connected to the reset input of an RS flip-flop 61. The set output Q of flip-flop 61 is connected to operate the switch 35 so that when flip-flop 61 is set by applying a +5 volts to the S input thereof from the decoder circuit as will be described, the CE electrode 33 in the electrochemical cell 19 is switched "on" and subsequently turned "off" when switch 1C is closed, resetting flip-flop 61. The programmed drum is advanced by means of a drive motor 63 which is an A.C. motor fed from an A.C. supply through a switch 65. Switch 65 is controlled by means of a J/K flip-flop 67 which has its J and K inputs connected to the +5 volt supply and a set output Q connected to the actuating input of switch 65. The motor 63 advances the program drum to operate the switches 1A through 11G by clock pulses from a clock pulse source 69 which are gated through a NAND gate 71. Gate 71 has a plurality of inputs which disable the clock pulses to be passed until the particular function that is to be performed at each position of the drum is completed. The output of NAND gate 71 is connected to the clock c input of flip-flop 67 which causes flip-flop 67 to be set each time a pulse appears at the c input, provided that the flip-flop 67 is cleared to the reset state following each program step. To stop the motor 63 a cam (not shown) is provided on the motor 63 shaft which operates a motor cam switch 73. Switch 73 has its common terminal connected to ground potential and the normally closed contact connected to the input of a one-shot multivibrator 75. The output of one-shot 75 is connected to the clear input of J/K flip-flop 67 so that when the motor completes rotation to advance the drum to the next position, switch 73 is released again applying ground to the normally closed input, thereby activating one-shot 75 which applies an output pulse to the clear input of J/K flip-flop 67 which resets flip-flop 67, turning motor 63 off. The motor 63 may be manually advanced by means of a push-button switch 77 which activates a one-shot 79 to apply a pulse to the preset input of flip-flop 67, thereby starting motor 63. The motor is stopped in the same manner as before by the release of cam switch 73.

To prevent false triggering of the D.C. flip-flops which decode the drum switch positions, the normally opened contact of cam switch 73 is connected to one input of an AND gate 81 whose output is connected to the c input of each of the D.C. flip-flops. The second input of AND gate 81 is connected to the output of a one-shot 83 whose input is connected to the output of one-shot 75. The output of one-shot 83 remains low following the release of the cam switch back to the normal position until the contacts have time to settle. When the one-shot 83 times out, the AND gate enables the D.C. flip-flops to allow the D inputs of flip-flops which have been activated by the new cam position to switch the output Q of the flip-flop accordingly.

The control logic stores the four different reduction current values measured for the electrochemical cell 19 in different memories 85, 87, 89, 90, shown in FIG. 5B. These memories are preferably conventional buffer storage units which store values from an analog-to-digital converter 91 which has an analog signal input connected to the output of the integrator 55, and a status line connected to one input of NAND gate 71. Timing control for the transfer of the digital signal from the ADC 91 and the signal to convert the analog input to ADC 91 to digital form is provided by means of decoder 93. Decoder 93 is a binary coded decimal decoder which has four inputs connected through corresponding inverters 95 to the Q outputs of D.C. flip-flops IIE, IID, IIC, and ID. According to the input code as decoded by means of Table II, referring to the program section I, the appropriate output line (0 through 7) is activated to provide particular control functions. The 0 output of the decoder 93 is connected to the reset R input of an RS flip-flop 97 which has its set input connected to the number 5 output of decoder 93. The set Q output of flip-flop 97 is connected to control the chlorine source 7, so that when line 5 of decoder 93 is activated, the flip-flop 97 is set turning the chlorine source "on;" and, subsequently, when the 0 line is activated, flip-flop 97 is reset turning the chlorine source "off." The number 1 output of decoder 93 is connected in common to enabling inputs of AND gates 99, 101, 103 and 104 which have outputs connected respectively to control inputs of memories 85, 87, 89 and 90. The particular memory that is selected is controlled by D.C. flip-flops IIA and IIB which have their Q set outputs connected to separate inputs of a data input memory decoder 105. Decoder 105 is also a binary coded decimal decoder which activates lines 0, 1, 2, and 3 according to the input code, as shown in Table II, section IV. Thus, output line 0 is connected to AND gate 104, output line 1 is connected to AND gate 99, output line 2 is connected to AND gate 101 and output line 3 is connected to AND gate 103. Further, the output lines of decoder 105 are connected to separate inputs of a timing logic control circuit 107. Control circuit 107 has a timing input connected to the output of the system clock 69 and depending upon which of the four inputs are activated the logic circuit 107 receives the clock pulses to provide four different timer periods by activating a particular one of the outputs 1 through 4 at the end of the selected time period. These outputs are connected through NOR gates 109 and 111 to separate inputs of NAND gate 71.

Once the proper values have been stored in memories 85, 87, 89, and 90, a calculation is done in analog form to obtain the air sample chlorine or chloride content. To make the calculation, digital-to-analog converters (DAC) 119, 121, 123, and 124 are connected, respectively, to the outputs of memories 85, 87, 89, and 90. The calculation is done according to the formulas as stated above where A or A' is the background, B is the $Cl_2$ or $(Cl_2 + Cl^-)$ in the air sample and C is the standard measurement with $Cl_2$ gas added. The output of DAC 121 is connected to one input of an analog subtracter 125 while the output of DAC 119, containing the $Cl_2$ background value, is connected through normally closed contacts of an electronic switch 126 to

TABLE II

| | Key To Programming Codes | | | | | |
|---|---|---|---|---|---|---|
| I. | PROGRAM (Decoder 93) Cam Actuated: X | | | | Function: | |
| | Inputs | | | | | Outputs |
| | I-D | II-C | II-D | II-E | | |
| X. | — | — | — | — | X. | NOOP |
| 0. | X | X | X | X | 0. | Turn off chlorine generator/ close valve |
| 1. | X | X | X | — | 1. | Transfer from ADC 91 to Memory |
| 2. | X | X | — | X | 2. | ADC 147 Convert ($Cl_2$ Panel Meter) |
| 3. | X | X | — | — | 3. | ADC 91 Convert |
| 4. | X | 1 0. | X | X | 4. | ADC 139 Convert and transfer to Memory 141 |
| 5. | X | — | X | — | 5. | Generate $Cl_2$ |
| 6. | X | — | — | X | 6. | ADC 133 Convert (chloride panel meter) |
| 7. | X | — | — | — | 7. | Connect Electrode CE |
| II. | INTEGRATOR (Decoder 113) | | | | | |
| | II-F | II-G | | | | |
| 0. | — | — | | | 0. | NOOP |
| 1. | — | X | | | 1. | Reset |
| 2. | X | — | | | 2. | Connect input to integrator |
| 3. | X | X | | | 3. | Integrate |
| III. | RECORDER (Decoder 157) | | | | | |
| | I-E | I-F | | | | |
| 0. | — | — | | | 0. | NOOP |
| 1. | — | X | | | 1. | Record $Cl_2$ value |
| 2. | X | — | | | 2. | Advance Chart, pen at zero |
| 3. | X | X | | | 3. | Record $Cl^-$ value |
| IV. | TIMER/MEMORY CODE (Decoder 105) | | | | TIMER | MEMORY(PROGRAM "X") |
| | II-A | II-B | | | | |
| 0. | — | — | | | 0. No. 1. | 0. Memory 90 |
| 1. | — | X | | | 1. No. 2 | 1. Memory 85 |
| 2 | X | — | | | 2. No. 3 | 2. Memory 87 |
| 3. | X | X | | | 3. No. 4 | 3. Memory 89 |

A Cam in I-G is an unconditional STOP for the drum; also disconnects electrode CE.
A Cam in I-A is a conditional STOP; used for Chlorine Only subroutine.
A Cam Maintained in position I-B turns on the air valve, stopping air flow. At least 30 seconds must be allowed between actuations of air valve.

To control the integrator 55 an additional decoder 113 is provided which has separate inputs connected to the Q outputs of D.C. flip-flops II-E and II-F. Integrator decoder 113 is identical to decoder 105 in that the particular binary code at the separate inputs is decoded to activate lines 0, 1, 2, or 3, to provide the function as indicated in section II of Table II. Line 1 of decoder 113 is connected to the set input of an RS flip-flop 115 and the number 3 line is connected to the reset input thereof. The set output Q of flip-flop 115 is connected to the reset/hold input of integrator 55. Line 2 of decoder 115 is connected to the set input of another RS flip-flop 117 which has its reset input connected to the number 2 timing output of timing logic controller 107. The set Q output of flip-flop 117 is connected to a relay K3. Relay K3 has one contact K3-A which connects the output of amplifier 51 to the input of the integrator 55.

the second input of subtracter 125. The common terminal of switch 126 is also connected to one input of another subtracter 127 which has its second input connected to the output of DAC 123. The normally open contact of switch 126 is connected to the output of DAC 124. The purpose of switch 126 is to select either the $Cl_2$ background value (A) or the $Cl^-$ background value (A').

The outputs of subtracter 125 and 127 are connected to separate inputs of an additional analog subtracter 129 which has its output connected to the F input of an analog divider 131. The D input of analog divider 131 is connected to the output of analog subtracter 125. The output of analog divider 131 which is the ratio D/F is connected to the input of analog multiplier 133 for appropriate scaling. The output of multiplier 133 is an analog signal proportional to the percent chlorine and is connected through relay contacts K1-A to one input of a dual-pen strip chart recorder 135. This is all the circuitry that is necessary to provide an output signal proportional to the chlorine value.

However, when it is desirable to also determine chloride values in the air sample, the output of analog divider 131 is connected to the input of an analog multiplier 137 whose output is connected to the input of analog-to-digital converter 139. The timing for the analog-to-digital conversion in converter 139 is controlled by the No. 4 output of decoder 93 which is connected to the control input of ADC 139 through a one-shot 140 and to the actuating input of switch 126. One-shot 140 delays the command pulse for a period sufficient to allow switching of the background value A' from DAC 124 to be subtracted in the analog circuit and the result appears at the input of ADC 139. When the conversion is complete, a status line is activated which is connected to the control input of an additional memory 141. The memory 141 has a data input connected to the output of ADC 139. The status line from ADC 139 is also connected to an input of NAND gate 71 which allows the motor to continue to the next step once the conversion is completed. The output of memory 141 is connected to a digital-to-analog converter 143 whose output is connected to one input of analog subtracter 145. To obtain the actual chloride value, it is necessary to subtract the value calculated for chlorine. Thus, the output of multiplier 133 is connected to the input of analog-to-digital converter 147 which is controlled from the decoder 93 by means of connecting the No. 2 line of decoder 93 to control input of ADC 147. The output of ADC 147 is connected to the input of a digital display unit 149. When the analog-to-digital conversion of ADC 147 is complete, a status line is activated which is connected to a control input of display 149 and further to separate input of NAND gate 71. Thus, the $Cl_2$ value is stored in display unit 149 and a digital output for the displayed value is provided to a digital-to-analog converter 151. The output of converter 151 is connected to a separate input of analog subtracter 145. The output of subtracter 145 provides a signal at an appropriate time which is proportional to the chloride value determined from the sample. This value is recorded on strip chart recorder 135 by closing contacts K2-A which connects the output of subtracter 145 to the input of recorder 135. To display the chloride value in a digital display, the output of subtracter 145 is connected to the input of an analog-to-digital converter 153. The control for this converter is provided by the No. 6 output line of decoder 93 which is connected to the control input of ADC 153. The status output line of ADC 153 is connected to a control input on the chloride display 155 and to an input of NAND gate 71 so that at the proper time sequence ADC 153 is activated and the converted value is stored in digital display 155 and the NAND gate 71 is again released to allow the clock pulses to step the motor 63 to the next drum position.

To control the recording of the $Cl_2$ and $Cl^-$ values in strip chart recorder 135, an additional decoder 157 is provided which is similar to decoders 105 and 113. The separate inputs are connected to Q outputs of flip-flops I-F and I-E. These inputs are decoded according to that shown in Table II, section 3, so that when the output line 1 of decoder 157 is activated, relay K1 is actuated to close contacts K1-A and record the $Cl_2$ value. At a different time the output line 3 of decoder 57 is actuated to pick up relay K2 which closes contacts K2-A recording the $Cl^-$ value in recorder 135. The strip chart is advanced by a signal on output line 2 of decoder 157 which is connected to the chart drive input of recorder 135. Further, the output line 2 of decoder 157 is connected to the No. 1 timer of timing logic circuit 107 to provide a delay, as will be described hereinbelow.

An additional selectable control function is provided by the cam switch 1A. If it is desirable to measure only the chlorine content, a switch 157, which is connected to a common terminal of switch 1A, may be set in one of two positions. In the position shown for switch 157, the program will continue through the entire process of measuring both chlorine and chloride values. However, if the switch 157 is set to the "$Cl_2$-only" position which is connected to ground, the programmer will skip the steps which are involved in calculating the chloride value. This skip operation is accomplished by overriding switch 73 with switch 1A to prevent gate 81 from being enabled until, at drum position "0" switch IA opens but is overridden momentarily by IG whereupon the drum stopping sequence described previously takes place.

The operation of the system may be most readily understood by referring to Table I in conjunction with FIG. 5. The analytical flow train is started by supplying the electrolyte flow through the cell 9 as described above. Then, assuming that the system has been "on" and preceeded through a complete cycle of steps 0 through 50, as shown in Table I, the 0 step disconnects the conditioning electrode CE by cam switch IC resetting flip-flop 61. Next the strip chart recorder 135 is advanced one step by means of closing contact IE and the timer 1 is activated through the activation of the No. 2 line of decoder 157. This causes the output No. 1 of timer 107 to go high, thus disabling the NAND gate 71 until the timing period expires by causing the output of NOR gate 109 to go low during the timer 1 period. When the timing period is over, the inputs to NAND gate 71 are at the high state and the next clock pulse produces a 1 for a period at an input of NAND gate 71 which causes the output to go low, thereby switching J/K flip-flop 67 to the set state. This applies an output to switch 65 which causes the motor to advance to the next position. This advance step is provided following the completion of each function specified by the drum program, and therefore will not be described following each of the descriptive steps. The motor is stopped to position the drum at the next position following each operation by the reset operation of one-shot 75 which disables motor switch 65. As described above, during each advance of the drum, the AND gate 81 disables all of the D.C. flip-flops connected to cam switches so that the data is not erroneously transferred to the decoders.

Next, in step 2, the switches ID and IID are activated which signals decoder 93 to set flip-flop 61 turning the chlorine gas source on. Following this operation the integrator 55 is reset by activating switches IIA and IIB. The activation of switches 11A and IIB acts through decoder 105 to provide a selected delay to allow the system to flush fresh electrolyte through by selecting line 3 of decoder 105. The integrator is reset by activating switch 11G at this position which acts through integrator decoder 113 to set flip-flop 115, resetting integrator 55. Next, according to step 4, switch IIF operates through decoder 113 to activate SR flip-flop 117 picking up relay K3 which connects the output of amplifier 51 to the integrator 55, keeping in mind that the integrator at this time is being held in the reset state. The integrator reset is released by activating switches IIF and IIG which operate through decoder 113 to reset flip-flop 115 releasing the reset/hold signal to integrator 55. Integration continues for a timing period activated by switch IIB which selects line 1 from decoder 105 to activate timer 2 of the timing logic 107 which then times out as an output at the No. 2 output which resets the flip-flop 117, dropping out relay K3.

Since the above measurement was made with inlet valve 57 open and the standard chlorine source 7 "on," the value measured is representative of the reduction current in the cell due to $Cl_2$ in the air sample plus that added by the standard chlorine source 7. This value is converted by analog-to-digital converter 91 by means of closing contacts IB and IIC. This is recognized by decoder 93 and activates output line 3 to sample the analog signal held in integrator 55 and converts it to digital form. Next, the chlorine generator is turned "off" as shown in Table I, step 8, and the value set in analog-to-digital converter 91 is transferred to memory 89. The integrator 55 is again reset and following a delay activated by closing contacts IIA and IIB. This selects line 3 of decoder 105 to activate the No. 3 timer in circuit 107, allowing the system to be flushed for the next step. The integrator is then connected and the value of chlorine in air without the standard chlorine source "on" is integrated over a period according to the setting of timer 2. Then the analog-to-digital converter 91 is again activated to convert this integrated value and the value is subsequently stored in memory 87. Keeping in mind that the system has progressed through a previous cycle, it will be understood that memory 85 has stored therein a value which is representative of the background chlorine value, i.e., the chlorine which is in the electrolyte solution and which would appear as an error in the readout. The values stored in memories 85, 87, and 89 at this time are representative of measured chlorine values in cell 19. Thus, the $Cl_2$ value at the next step is present at the output of analog multiplier 133 and is recorded on the strip chart 135 by closing contacts K1-A. This is accomplished by step 15 as shown in Table I. Contact IF is closed which activates line 1 of the decoder 157 to pick up relay K1.

Referring back to the formula for calculating chlorine from the stored values, it will be seen that the digital-to-analog converters 119, 121, and 123 convert the stored values to analog form and the background value stored in memory 85 (A) is subtracted from both the value (B) and the value (C). The output of subtracter 125 is a value (D) which is supplied to the D input of divided 131 while the output of subtracter 137 is a value (E). Value (D) is subtracted from value (E) in analog subtracter 129 to obtain the value (F) to the F input of analog divider 131. The ratio (E/F) is multiplied by a scaling factor at 133. The factor K1 is determined by initial standardization procedures involving the introduction of air samples containing known amounts of chlorine and a specific form of cell 19, i.e., the surface area of exposed platinum electrode 37. Thus, the output of multiplier 131 at this time is an analog signal indicative of the chlorine (PPM) in the air sample entering the analyzer through the inlet air valve 57. This value is converted to digital form by ADC 147 and stored in $Cl_2$ digital display 149. This completes the calculation and display of the chlorine content of the incoming air.

To determine the background values for the electrolyte, the air is turned "off" by activating contact IB. Contact IB stays closed from step 17 through step 30 to make the background measurement as follows. A delay time is activated by closing contacts IIG which allows the system to again flush and the integrator is reset by closing contacts IIA and IIB, as explained above. Next the integrator input is connected by closing contact IIF and an integration period begins for a timer 3 period. This integration provides the background chlorine content and is converted by analog-to-digital converter 91 and subsequently stored in memory 85 as the value (A).

Step 25, Table I, starts the background measurement for the chloride value. The chloride is measured by first oxidizing chloride to chlorine and measuring the reduction current by reducing the generated chlorine to chloride again. To do this, the CE electrode is connected by closing contact IB. A delay is initiated by operating timer 2 of the timing logic control 107 by activating switch IIB according to step 27. This delay allows the system to again be flushed before the measurement of the $Cl_2$ reduction current. Then, the integrator 55 is connected by activating relay K3 and the integrator is again started by releasing the reset and setting timer 3 in the timing logic 107. After the timer 3 times out and the drum steps to the next step (30), the integrated value is converted and stored in memory 90 as value A', and the integrator 55 is again reset. This completes the storage of the background values in the appropriate memories.

At this point, step 32 in the drum program, contact IA is closed. Depending upon the position of the switch 157, the system will either skip step 32 through step 50 and go back to step 0, or continue with the steps 32 through 50. If switch 157 is set to read chlorine values only, the closing of switch IA activates the skipping of steps 32 through 50 and the drum rotates to the 0 position and begins a new cycle, as will be explained hereinbelow. However, if the switch 157 is in the normal position, the system progresses to measure the chloride content in the incoming air. As is shown by contact IIB being opened in steps 31 through 50, the air again enters the system for this measurement. Electrode CE is connected to condition the input chloride in air converting chloride to chlorine. The integrator 55 is reset in the same manner as described above, and connected to the output of amplifier 51. A delay is activated as described above to flush the system prior to the integrating step for determining the chlorine contribution by both chloride which is oxidized and the chlorine which is already present in the air sample. Then the integrator reset is released and the timer 4 is activated in the timing logic 107 so that the integrator 55 proceeds to integrate the reduction current value equivalent to ($Cl^- + Cl_2$) in the air sample. At the end of the timer period 4 the analog-to-digital converter 91 is signalled to convert the integrated value and the next step, drum position 37, the converted value is stored in memory 87. The integrator 55 is reset also by this step and the chlorine generator is turned "on" by closing contacts ID and IID. After another delay period, the integrator is again connected and subsequently integration begins at step 42 for a timer period 4. Following the integration, this value is converted by signalling converter 91 and subsequently stored in memory 89.

The value now stored in memory 89 is indicative of the total chlorine in the air sample. At this point the second calculation is made according to the formula above for determining chloride in the following manner. The analog portion of the circuit does the same function as described above with the exception that this time the output of the analog divider 131 is recognized at the input of the analog-to-digital converter 139 through the different scale factor multiplying circuit 137. According to step 46 program as shown in Table I, the analog-to-digital converter 139 is activated at this time by closing contacts ID, IID, and IIE to activate line 4 of the decoder 93. This signal activates switch 126 to introduce the chloride background value (A') into the analog system; and after a delay by one-shot 140 signals analog converter 139 to convert. Following the conversion, a signal is presented at the control output which signals memory unit 141 to store the converted value. Thus, the value for the total chlorine including chlorine and/or chloride is now stored in the memory 141. Next, the recorder is advanced by activating contact IE to prepare for the chart recording of chloride analog signal. Recalling that the chlorine value which is set in the display 149 must be subtracted to obtain the actual chloride value, the output from the display 149 is converted at the digital-to-analog converter 151 and subtracted from the value stored in memory 141 by analog subtracter 145. Thus, the analog signal at the output of subtracter 145 is proportional to the chloride measurement and this is supplied to the chart recorder 135 by closing contacts K2-A. This is accomplished by the drum closing contacts IE and IF which activates decoder 157 to select the NO. 3 output line, activating relay K2. As shown by steps 48 and 49 in the program, the chloride value may be recorded twice in parallel to provide a thicker line than the recording of the chlorine values to readily distinguish the two values. Finally, the chloride value is presented to digital display 155 by activating analog-to-digital converter 153. This is accomplished by closing contacts ID and IIE which select output line 6 of the decoder 93. This signals ADC 153 to convert the analog chloride value to digital form and present it to the input of the display 155. When the conversion is completed, the control line is activated which triggers the record control to the input of display 155 and further signals through NAND gate 71 to advance the drum by activating motor 63. The drum continues to the home position "0". Thus, it will be seen that the values for chlorine and chloride in the air entering through the inlet valve 57 of the analyzer train are calculated and recorded automatically and the system continues the cycle until some malfunction signals a stop or the system is stopped for maintenance or replenishing the electrolyte.

The monitoring system may include branch points which are selected by front panel controls (not shown) to allow the system to skip various steps, such as determining the background values for measurements of rather high chlorine or chloride concentration levels. Since the correction for background current is small at high concentrations of halogens, provisions may be made to automatically circumvent the background measurement 9 out of 10 times when a range of 0.1 part per million or higher is selected. Below this concentration level, a background correction is stored on each cycle as explained above. A second branch point allows the chloride routine to be skipped as pointed out above. This may be accomplished by triggering a decade counter each cycle so that once in each ten cycles the counter overflows to trigger a background measurement.

One important feature of the monitor is the system of calibration. In a flowing system it is virtually impossible to provide a quantitative standardization. In this case, the difficulty is multiplied by the high vapor pressure and corrosiveness of $Cl_2$ and hydrochloric acid. Thus, chlorine is generated at constant current from an acidified chloride solution. This is accomplished by the standard chlorine source 7. The incoming air sweeps the chlorine from a platinum anode. The chloride is then seen as part of the sample. By treating the standard in the same way as the sample is processed, the overall efficiency for the recovery of chlorine can be assessed and the absolute concentration of chlorine in the sample quantified. Since chlorides are determined ultimately as chlorine only one calibration gas is needed. This form of calibration has the added advantage that the temperature regulation is not required for the chlorine source.

The system provides a linear response to both species in the range of from about 10 to 1000 parts per billion chlorine and/or chloride in the incoming air sample.

In the first work with the monitor, only $H_2SO_4$ was used as an absorber. With this absorber solution, hydrochloric acid is readily removed from the air sample. On the other hand, while chlorine is quite soluble in 6 M $H_2SO_4$, the rate of absorption is slow. With $2 \times 10^{-3}$ M NaOH as the absorbing solution, both species are absorbed. When only one solution is used, it is possible to aspirate it reproducibly into the absorption coil. With the two solution absorbers, it is necessary to pump the solution by positive displacement in order to firstly adjust the ratio conveniently, and secondly, to maintain a constant ratio of sodium hydroxide to sulfuric acid. With the sodium hydroxide absorber $CO_2$ is also scavenged. Flow of electrolyte through the cell is by gravity. It is sometimes interrupted by gas bubbles in the cell arising from $CO_2$ escaping from the acidified electrolyte. The problem is eliminated by introducing the sulfuric acid prior to the last two turns of the absorption tube as shown in FIG. 4. Thus, it will be seen that a very efficient and reliable automated system has been provided to monitor chlorine and/or chloride in the atmosphere on a continuous basis which does not require ion-specific electrodes.

What is claimed is:

1. A system for electrochemical monitoring of the chlorine and/or chloride level in atmospheric air mixed with a flowing electrolyte, comprising:

a flow-through electrochemical cell disposed to receive said flowing electrolyte including a conditioning electrode disposed in said cell for contacting said flowing electrolyte entering said cell, an analytical electrode disposed to contact said flowing electrolyte downstream of said conditioning electrode, a reference electrode disposed to contact said flowing electrolyte downstream of said analytical electrode, and a counter electrode disposed to contact said flowing electrolyte downstream of said reference electrode;

an absorber connected in fluid communication with the flow-receiving end of said cell;

means connected in fluid communication with said absorber for introducing said electrolyte into said absorber at a predetermined flow rate;

means for selectively introducing air at a controlled flow rate into said absorber wherein the chlorine and/or chloride content is sorbed by said electrolyte;

a standard chlorine source disposed to generate and introduce upon command chlorine gas at a predetermined rate into the air flow upstream of said absorber;

means connected to said electrodes for applying a positive direct voltage between said reference electrode and said analytical electrode to effect reduction of chlorine sorbed in said electrolyte flowing through said cell and selectively applying upon command a greater positive voltage between said reference electrode and said conditioning electrode to provide oxidation of chloride sorbed in said electrolyte flowing through said cell which is subsequently reduced to chlorine at said analytical electrode; and process control means responsive to a repeating programmed schedule for controlling the introduction of chlorine gas from said standard chlorine source selectively actuating said conditioning electrode and sensing the reduction currents flowing through said counter electrode indicative of the chlorine concentration in said cell for different periods when said chlorine source is "on" and "off" and said conditioning electrode is activated or inactivated to separately determine and indicate the chlorine and/or chloride level content in the air introduced into said system.

2. The system as set forth in claim 1 wherein said electrodes are platinum.

3. The system as set forth in claim 2 further including a debubbler chamber disposed in the electrolyte flow line between said absorber and said cell for removing unsorbed gases from said electrolyte prior to introduction of the electrolyte into said cell.

4. An automatic electrochemical monitoring system as set forth in claim 3 wherein said process control means includes a signal integrator coupled to said counter electrode, an analog-to-digital converter connected to the output of said integrator, a plurality of digital storage means connected to the output of said analog-to-digital converter for separately storing integrated signals indicative of said reduction current values in said cell, a programmable control means for resetting said integrator prior to each reduction current measurement and controlling the transfer of said integrated values over a selected time period into separate ones of said plurality of storage means, and means responsive to values stored in said storage means for computing and storing the chlorine level in the air introduced into said system by determining the ratio of the stored value when said chlorine source is "off" to the stored value when said chlorine source is "on".

5. The system as set forth in claim 4 wherein said process control means further including means for computing and storing the chloride level in the air introduced into said system by determining the ratio of the stored values for said chlorine source "on" to the stored value for said chlorine source "off" when said conditioning electrode is activated and subtracting said chlorine level.

6. The system as set forth in claim 5 wherein said process control means further includes means for controlling the storage of values in separate ones of said storage means indicative of the background chlorine and/or chloride in the electrolyte in said system for correcting the corresponding level measurement computations by subtracting the background value from each of said stored reduction current values.

* * * * *